(12) United States Patent
Xin et al.

(10) Patent No.: US 9,587,198 B2
(45) Date of Patent: *Mar. 7, 2017

(54) MANNICH BASE, PRODUCTION AND USE THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Shihao Xin, Beijing (CN); Qinghua Duan, Beijing (CN); Zuoxin Huang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 26 days.

This patent is subject to a terminal disclaimer.

(21) Appl. No.: 14/397,335

(22) PCT Filed: Apr. 25, 2013

(86) PCT No.: PCT/CN2013/000473
§ 371 (c)(1),
(2) Date: Oct. 27, 2014

(87) PCT Pub. No.: WO2013/159570
PCT Pub. Date: Oct. 31, 2013

(65) Prior Publication Data
US 2015/0121747 A1 May 7, 2015

(30) Foreign Application Priority Data
Apr. 26, 2012 (CN) .......................... 2012 1 0127904

(51) Int. Cl.
C10M 133/54 (2006.01)
C10M 159/16 (2006.01)
(Continued)

(52) U.S. Cl.
CPC ......... *C10M 133/54* (2013.01); *C07C 215/50* (2013.01); *C08F 110/10* (2013.01);
(Continued)

(58) Field of Classification Search
CPC .............. C10M 133/54; C10M 159/16; C10M 2215/26; C10M 2217/043; C10L 1/2366;
(Continued)

(56) References Cited

U.S. PATENT DOCUMENTS 3,736,357 A * 5/1973 Piasek et al. ......... C07C 275/14
508/542
4,242,212 A 12/1980 Hanson
(Continued)

FOREIGN PATENT DOCUMENTS

CN 1197835 A 11/1998
CN 1230561 A 10/1999
(Continued)

OTHER PUBLICATIONS

International Search Report dated Aug. 1, 2013 issued in International Application No. PCT/CN2013/000473.
(Continued)

*Primary Examiner* — James Goloboy
(74) *Attorney, Agent, or Firm* — Scully Scott Murphy & Presser

(57) ABSTRACT

This invention relates to a Mannich base, production and use thereof in producing a detergent. The Mannich base is represented by the following formula (III), wherein A and $R_2$ are as defined in the specification. The Mannich base can be
(Continued)

used to produce a detergent and a fuel oil composition exhibiting excellent deposit formation suppressing performance and excellent anticorrosion performance.

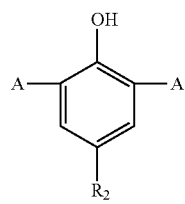

(III)

13 Claims, 4 Drawing Sheets

(51) Int. Cl.
C07C 215/50 (2006.01)
C10L 1/236 (2006.01)
C10L 1/238 (2006.01)
C10L 10/04 (2006.01)
C11D 3/37 (2006.01)
C11D 3/30 (2006.01)
C08F 110/10 (2006.01)

(52) U.S. Cl.
CPC ............. *C10L 1/238* (2013.01); *C10L 1/2366* (2013.01); *C10L 10/04* (2013.01); *C10M 159/16* (2013.01); *C11D 3/30* (2013.01); *C11D 3/3723* (2013.01); *C10L 2200/0423* (2013.01); *C10L 2200/0446* (2013.01); *C10L 2250/04* (2013.01); *C10M 2215/26* (2013.01); *C10M 2217/043* (2013.01); *C10N 2230/04* (2013.01)

(58) Field of Classification Search
CPC .. C10L 1/238; C10L 10/04; C10L 2200/0423; C10L 2200/0446; C10L 2250/04; C11D 3/30; C11D 3/3723; C10N 2230/04; C07C 215/50; C08F 110/10
USPC .................................................. 508/200, 542
See application file for complete search history.

(56) References Cited

U.S. PATENT DOCUMENTS

| 5,039,307 A | 8/1991 | Herbstman et al. |
| 5,608,029 A * | 3/1997 | Thaler .................. C07D 233/02 508/558 |
| 5,725,612 A | 3/1998 | Malfer et al. |
| 6,015,863 A | 1/2000 | Mike et al. |
| 2004/0168364 A1* | 9/2004 | Macduff .................. C08F 8/32 44/415 |
| 2007/0169408 A1 | 7/2007 | Hou et al. |
| 2008/0141583 A1 | 6/2008 | Malfer et al. |
| 2009/0094887 A1 | 4/2009 | Calvert et al. |

FOREIGN PATENT DOCUMENTS

| CN | 1351132 A | 5/2002 |
| CN | 1541200 A | 10/2004 |
| CN | 1720317 A | 1/2006 |
| CN | 101058761 A | 10/2007 |
| CN | 101067097 A | 11/2007 |
| CN | 101126039 A | 2/2008 |
| CN | 102516097 A | 6/2012 |
| EP | 1 375 629 A2 | 1/2004 |
| EP | 1 712 605 A1 | 10/2006 |
| WO | WO 02/30471 A2 | 4/2002 |

OTHER PUBLICATIONS

European Search Report issued in corresponding European Patent Appln. No. 13781793.8, dated Apr. 4, 2016.
International Search Report dated Aug. 1, 2013 issued in International Application No. PCT/CN2013/000474.
Japanese Office Action dated Nov. 29, 2016 issued in JP 2015-507343.

* cited by examiner

MANNICH BASE, PRODUCTION AND USE THEREOF

TECHNICAL FIELD

This invention relates to a Mannich base, especially relates to a Mannich base suitable for producing a detergent. This invention further relates to production and use of the Mannich base for producing a detergent.

BACKGROUND ART

Unsaturated olefins, aromatics and minor amounts of sulfur-containing compounds in the fuel oil tend to form gums by reacting with oxygen, and ultimately to form carbon deposits, especially at critical locations like intake valves, nozzles, or the combustion chamber, which will facilitate formation of engine deposits and seriously affect the performance of the engine, causing engine problems like difficult starting, idle instability, poor driving, poor acceleration, and severe power loss. In order to suppress the formation of such deposits in the engine, the prior art has developed a number of detergents. U.S. Pat. No. 5,725,612 discloses a Mannich base and a process for producing same. The Mannich base is produced by reacting a hydrocarbyl-substituted alkyl o-cresol with an aldehyde and an amine, and after produced into a detergent, exhibits some deposit formation suppressing performance.

US 20040168364 discloses a Mannich base and a process for producing same. The Mannich base is produced by the reaction of a phenolic compound with an aldehyde and an amine, and after produced into a detergent, exhibits some deposit formation suppressing performance.

However, there still remains much room for the prior art detergent to be improved in terms of the deposit formation suppressing performance.

In addition to the adverse effects of deposit, rust on engines will seriously shorten the service life of engine, and that on some key parts will largely affect the operating performance of engine. The prior art pays a lot of attention on the deposit formation suppressing performance of a detergent, but little on the anticorrosion performance thereof.

Therefore, there still remains a need in the prior art for a detergent, which can effectively suppress the formation of deposits, and at the same, shows excellent anticorrosion performance.

INVENTION SUMMARY

The present inventors, on the basis of the prior art, found a novel Mannich base, and further found that, by using the Mannich base as the major agent in the production of a detergent, the aforesaid problems encountered by the prior art can be solved, and then this invention is achieved.

Specifically, this invention relates to the following aspects.

1. A Mannich base, comprising the structure unit (I) and the structure unit (II):

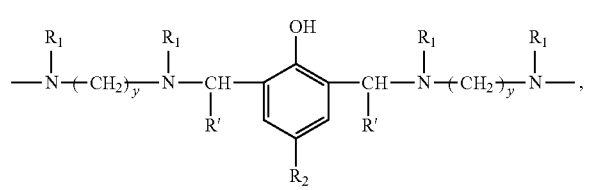

(I)

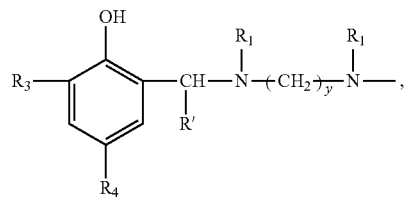

(II)

wherein, multiple $R_1$ may be the same as or different from one another, each independently selected from the group consisting of hydrogen, a $C_{1-4}$ linear or branched alkyl and a single bond, preferably each independently selected from the group consisting of hydrogen, methyl and a single bond, more preferably each independently selected from the group consisting of hydrogen and a single bond; multiple R' may be the same as or different from one another, each independently selected from the group consisting of hydrogen and a $C_{1-6}$ linear or branched alkyl, preferably each independently selected from the group consisting of hydrogen and methyl, more preferably hydrogen; $R_2$ represents a $C_{1-12}$ linear or branched alkyl, more preferably a $C_{5-12}$ linear or branched alkyl; $R_3$ represents a $C_{1-6}$ linear or branched alkyl, preferably a $C_{1-4}$ linear or branched alkyl, more preferably methyl; $R_4$ represents a hydrocarbyl having a number-averaged molecular weight Mn of 300-3000 (preferably 500-2000, more preferably 500-1500); multiple y may be the same as or different from one another, each independently selected from an integer of from 2 to 5, preferably 2 or 3.

2. The Mannich base according to any of the proceeding aspects, represented by the following formula (III):

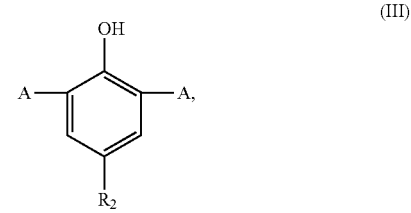

(III)

wherein, multiple A may be the same as or different from one another, each independently selected from the group consisting of

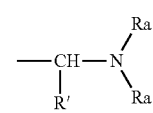

and hydrogen, preferably

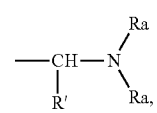

with the proviso that at least one A represents

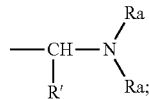

multiple R' may be the same as or different from one another, each independently selected from the group consisting of hydrogen and a $C_{1-6}$ linear or branched alkyl, preferably each independently selected from the group consisting of hydrogen and methyl, more preferably hydrogen; multiple $R_a$ may be the same as or different from one another, each independently selected from the group consisting of hydrogen, a $C_{1-4}$ linear or branched alkyl and

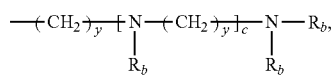

preferably each independently selected from the group consisting of hydrogen, methyl and

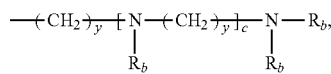

more preferably each independently selected from the group consisting of hydrogen and

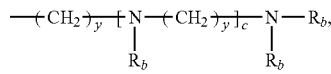

with the proviso that at least one $R_a$ represents

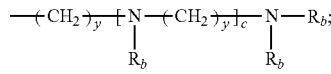

multiple $R_b$ may be the same as or different from one another, each independently selected from the group consisting of hydrogen,

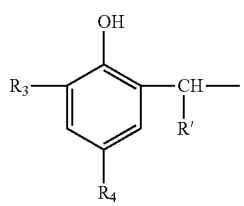

and a $C_{1-4}$ linear or branched alkyl, preferably each independently selected from the group consisting of hydrogen,

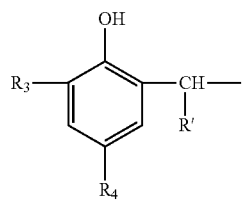

and methyl, more preferably each independently selected from the group consisting of hydrogen and

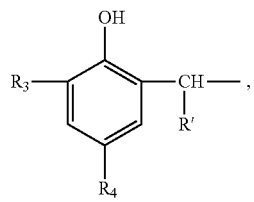

with the proviso that at least one $R_b$ represents

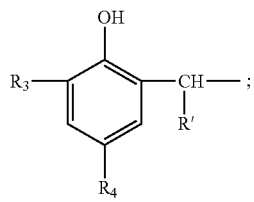

$R_2$ represents a $C_{1-12}$ linear or branched alkyl, more preferably a $C_{5-12}$ linear or branched alkyl; $R_3$ represents a $C_{1-6}$ linear or branched alkyl, preferably a $C_{1-4}$ linear or branched alkyl, more preferably methyl; $R_4$ represents a hydrocarbyl having a number-averaged molecular weight Mn of 300-3000 (preferably 500-2000, more preferably 500-1500); multiple y may be the same as or different from one another, each independently selected from an integer of from 2 to 5, preferably 2 or 3; multiple c may be the same as or different from one another, each independently selected from an integer of from 0 to 10, preferably each independently selected from an integer of from 2 to 5, more preferably 2 or 3.

3. A process for producing a Mannich base comprising the step of reacting a phenolic compound of the formula (V), a phenolic compound of the formula (VI), a polyalkylenepolyamine of the formula (VII) and a $C_1$-$C_7$ linear or branched saturated aliphatic aldehyde (preferably acetaldehyde or formaldehyde, more preferably formaldehyde, especially in the form of aqueous formaldehyde solution, polyformaldehyde or paraformaldehyde) to conduct a Mannich reaction,

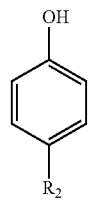

(V)

-continued $$\underset{(VI)}{\underset{R_4}{\underset{|}{\overset{OH}{\underset{|}{\bigcirc}}}}-R_3}$$

$$R'_b-\underset{R'_b}{\underset{|}{N}}-(CH_2)_y\underset{c'}{\underset{}{}}\underset{R'_b}{\underset{|}{N}}-R'_b \quad (VII)$$

wherein, $R_2$ represents a $C_{1-12}$ linear or branched alkyl, more preferably a $C_{5-12}$ linear or branched alkyl; $R_3$ represents a $C_{1-6}$ linear or branched alkyl, preferably a $C_{1-4}$ linear or branched alkyl, more preferably methyl; $R_4$ represents a hydrocarbyl having a number-averaged molecular weight Mn of 300-3000 (preferably 500-2000, more preferably 500-1500); multiple $R_b'$ may be the same as or different from one another, each independently selected from the group consisting of hydrogen and a $C_{1-4}$ linear or branched alkyl, preferably each independently selected from the group consisting of hydrogen and methyl, more preferably hydrogen, with the proviso that at least two of $R_b'$ are hydrogen, more preferably at least one of the multiple $R_b'$ at each terminal of the molecular chain of the polyalkylenepolyamine of the formula (VII) represents hydrogen; y represents an integer of from 2 to 5, preferably 2 or 3; c' represents an integer of from 1 to 11, preferably an integer of from 3 to 6, more preferably 3 or 4.

4. The process for producing a Mannich base according to any of the proceeding aspects, which is conducted in line with any one of the following ways:

Way (1) comprising the following steps:

the first step: reacting the phenolic compound of the formula (VI), the polyalkylenepolyamine of the formula (VII) and the $C_1$-$C_7$ linear or branched saturated aliphatic aldehyde at a reaction temperature of 50 to 200 degrees centigrade (preferably 60 to 150 degrees centigrade, most preferably 80 to 130 degrees centigrade) to conduct a Mannich reaction, to produce an intermediate; and the second step: reacting the intermediate, the phenolic compound of the formula (V) and the $C_1$-$C_7$ linear or branched saturated aliphatic aldehyde at a reaction temperature of 40 to 200 degrees centigrade (preferably 60 to 150 degrees centigrade, most preferably 80 to 130 degrees centigrade) to conduct a Mannich reaction, so as to produce the Mannich base, or Way (2) comprising the following steps:

the first step: reacting the phenolic compound of the formula (V), the polyalkylenepolyamine of the formula (VII) and the $C_1$-$C_7$ linear or branched saturated aliphatic aldehyde at a reaction temperature of 40 to 200 degrees centigrade (preferably 60 to 150 degrees centigrade, most preferably 80 to 130 degrees centigrade) to conduct a Mannich reaction, to produce an intermediate; and the second step: reacting the intermediate, the phenolic compound of the formula (VI) and the $C_1$-$C_7$ linear or branched saturated aliphatic aldehyde at a reaction temperature of 50 to 200 degrees centigrade (preferably 60 to 150 degrees centigrade, most preferably 80 to 130 degrees centigrade) to conduct a Mannich reaction, so as to produce the Mannich base, or Way (3) comprising the step of reacting the phenolic compound of the formula (V), the phenolic compound of the formula (VI), the polyalkylenepolyamine of the formula (VII) and the $C_1$-$C_7$ linear or branched saturated aliphatic aldehyde at a reaction temperature of 40 to 200 degrees centigrade (preferably 60 to 150 degrees centigrade, most preferably 80 to 130 degrees centigrade) to conduct a Mannich reaction to produce the Mannich base.

5. The process for producing a Mannich base according to any of the proceeding aspects, wherein in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.3-3:0.3-3.5, preferably 1:0.4-2:0.4-2.5, more preferably 1:0.5-1.5:0.5-2; in the second step of Way (1), the ratio by molar between the intermediate, the phenolic compound of the formula (V) and the $C_1$-$C_7$ linear or branched saturated aliphatic aldehyde is 1:0.2-1.5:0.2-2, preferably 1:0.3-1:0.2-1.5, more preferably 1:0.3-0.8:0.3-1.5; in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.5-2.5:1.5-3, preferably 1:1.7-2.5:1.7-2.8, more preferably 1:1.7-2.2:1.7-2.5; in the second step of Way (2), the ratio by molar between the intermediate, the phenolic compound of the formula (VI) and the $C_1$-$C_7$ linear or branched saturated aliphatic aldehyde is 1:1.5-3:1.5-3, preferably 1:1.7-2.5:1.7-3, more preferably 1:1.7-2.3:1.7-2.5; in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1-5:1-3:2-8, preferably 1:1.5-4.5:1.5-2.5:3-7, more preferably 1:1.8-4.3:1.8-2.3:3.5-6.5.

6. The process for producing a Mannich base according to any of the proceeding aspects, wherein the Mannich reaction is conducted in the presence of one or more diluent selected from the group consisting of polyolefins, mineral base oils and polyethers.

7. The process for producing a Mannich base according to any of the proceeding aspects, wherein the phenolic compound of the formula (VI) is produced by in the presence of an alkylating catalyst, reacting a phenolic compound of the formula (IV) with a polyolefin having a number-averaged molecular weight Mn of 300-3000 (preferably 500-2000, more preferably 500-1500) to conduct an alkylation reaction, wherein the polyolefin is preferably produced by the homopolymerization of ethylene, propylene or a $C_4$-$C_{10}$ α-olefin or by the copolymerization between two or more of these olefins, more preferably polyisobutene, $$\underset{(IV)}{\underset{}{\overset{OH}{\underset{}{\bigcirc}}}-R_3},$$

wherein, $R_3$ is as defined in the aspect 3.

8. A detergent comprising the Mannich base according to any of the proceeding aspects or a Mannich base produced in line with the process according to any of the proceeding aspects, and optionally one or more diluent selected from the group consisting of polyolefins, mineral base oils and polyethers.

9. The detergent according to any of the proceeding aspects, wherein by weight, the Mannich base accounts for 10-70%, preferably 10-60%, most preferably 10-50%, of the total weight of the detergent.

10. A fuel oil composition, comprising the Mannich base according to any of the proceeding aspects, a Mannich base produced in line with the process according to any of the proceeding aspects or the detergent according to any of the proceeding aspects, and a base fuel, wherein calculated as the Mannich base, on the basis of the total weight of the fuel oil composition, the amount of the Mannich base or the detergent is 30-2000 mg/kg, preferably 50-2000 mg/kg, more preferably 50-1000 mg/kg.

Technical Effects

According to this invention, with this novel Mannich base, a detergent with excellent deposit formation suppressing performance and excellent anticorrosion performance can be produced.

According to this invention, with the thus produced detergent, a fuel oil composition with excellent deposit formation suppressing performance and excellent anticorrosion performance can be produced.

FIGURE DESCRIPTION

Figure 3:
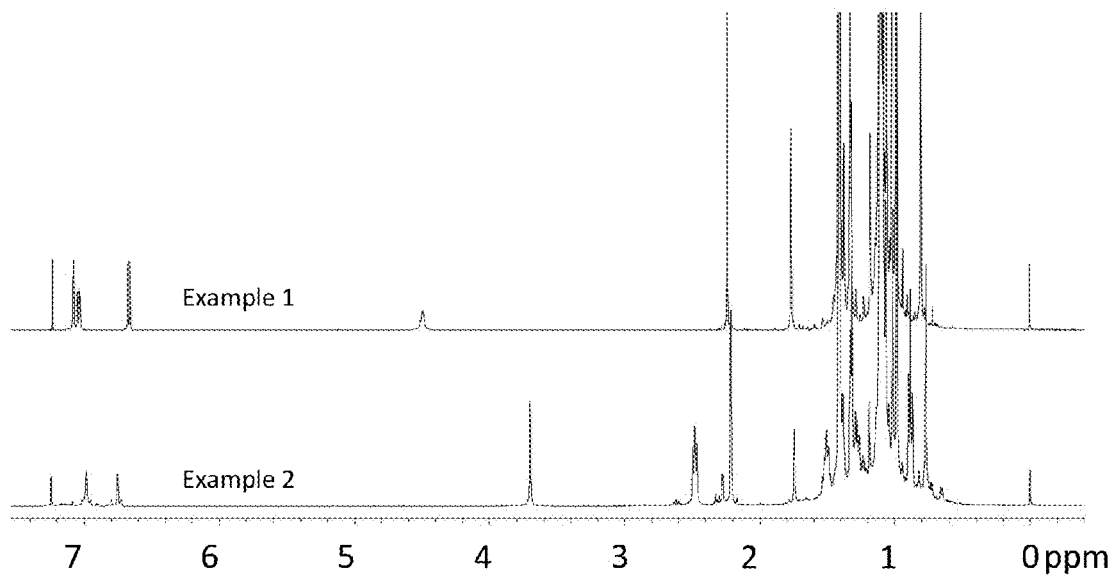

FIG. 3 compares the 1H NMR spectrum of the Mannich base produced in Example 2 with that of the polyisobutenyl o-cresol produced in Example 1.

Figure 4:
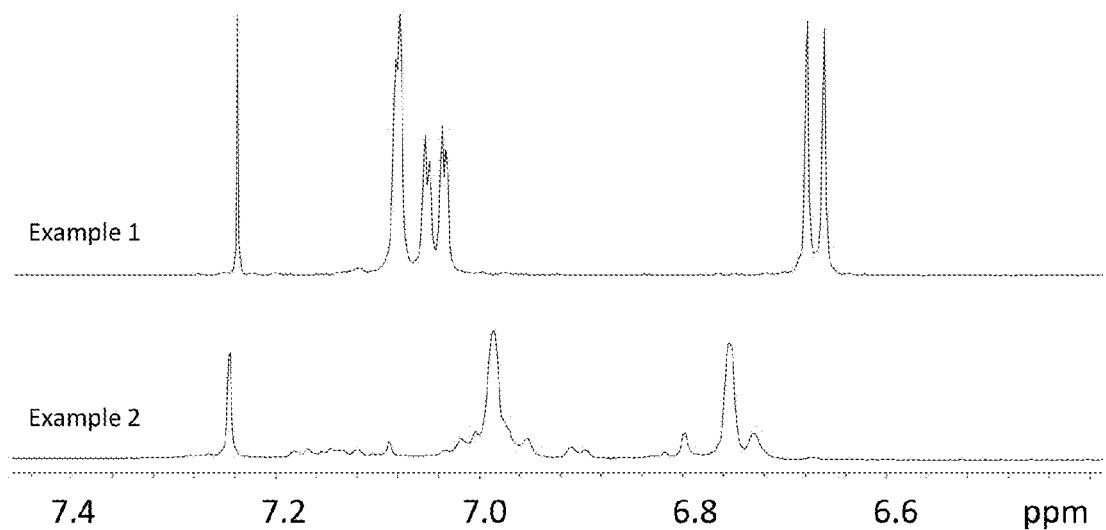

FIG. 4 compares the benzene ring region in the 1H NMR spectrum of the Mannich base produced in Example 2 and that of the polyisobutenyl o-cresol produced in Example 1.

Figure 5:
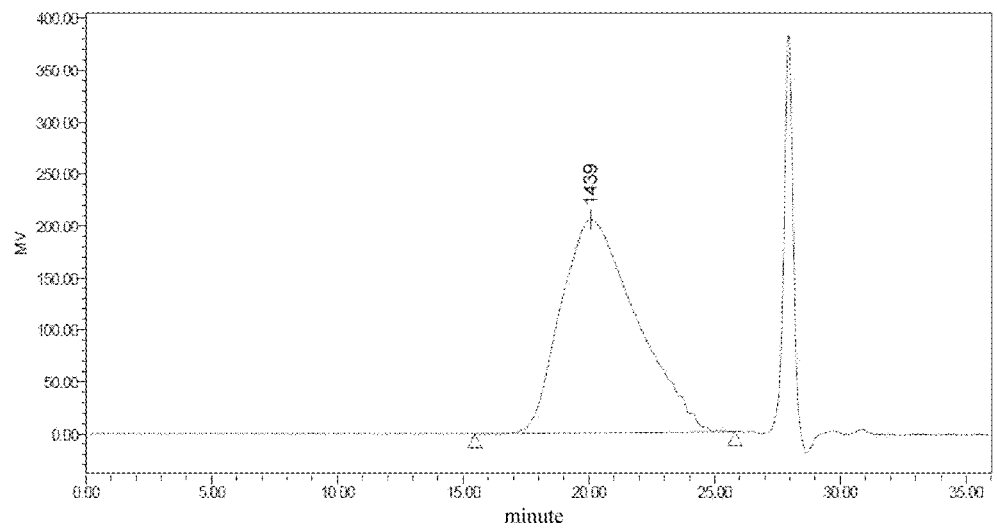

FIG. 5 illustrates the GPC spectrum of the polyisobutenyl o-cresol produced in Example 1.

Figure 6:
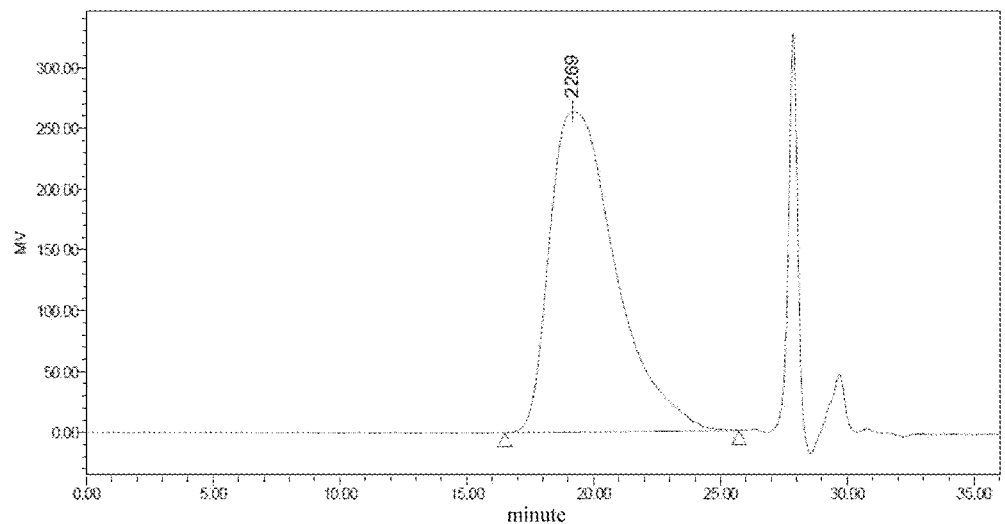

FIG. 6 illustrates the GPC spectrum of the Mannich base produced in Example 2.

Figure 7:
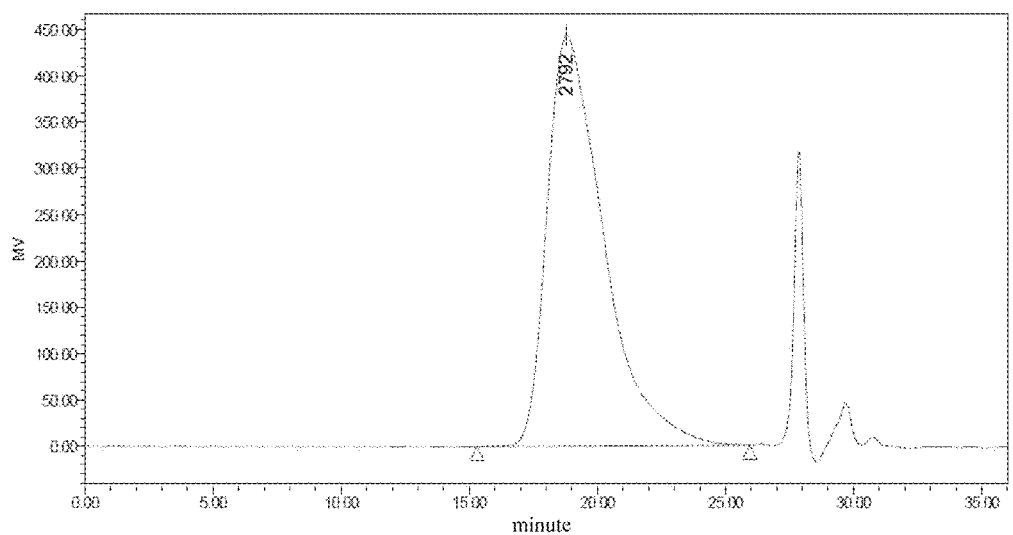

FIG. 7 illustrates the GPC spectrum of the Mannich base produced in Example 5.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, comprising any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern. In the context of this invention, when an expression like "conventionally known in this field" or "conventionally used in this field" or the like is used to describe/define an item like a material, a process, a part, an apparatus or a device, it means that this item (1) has been well known for a similar purpose in this field before this application, or (2) has not been that much well known for a similar purpose in this field before this application but gets well known for a similar purpose in this field after this application.

Unless otherwise specified, percents, parts or ratios or the like mentioned in this specification are all on a weight basis.

In the context of this specification, unless otherwise specified, the number-average molecular weight (Mn) is determined by gel permeation chromatography (GPC). In the context of this specification, unless otherwise specified, the gel permeation chromatography is performed on Waters 2695 Gel Permeation Chromatograph (from Waters, USA), with a mobile phase of tetrafuran, a flow rate of 1 mL/min, a column temperature of 35 degrees Celsius, an elution time of 40 min, and a weight fraction of the sample of from 0.16% to 0.20%.

According to this invention, related to is a Mannich base comprising the structure unit (I) and the structure unit (II):

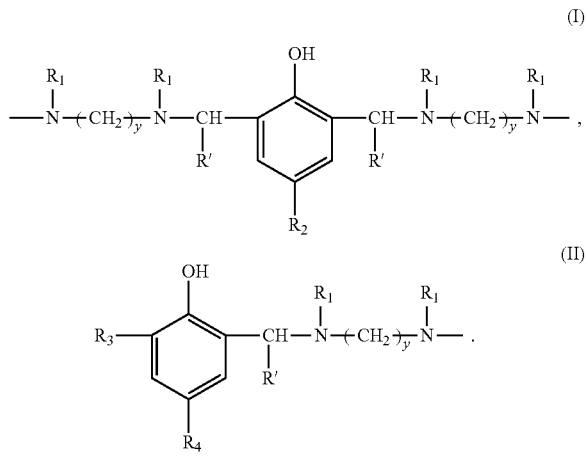

In these structure units, multiple $R_1$ may be the same as or different from one another, each independently selected from the group consisting of hydrogen, a $C_{1-4}$ linear or branched alkyl and a single bond; multiple R' may be the same as or different from one another, each independently selected from the group consisting of hydrogen and a $C_{1-6}$ linear or branched alkyl; $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5.

According to this invention, multiple $R_1$ is preferably each independently selected from the group consisting of hydrogen, methyl and a single bond, more preferably each independently selected from the group consisting of hydrogen and a single bond.

According to an embodiment of this invention, as for the p-alkyl phenol unit at the center of the structure unit (I), it is preferred that one of the two $R_1$ on the left side thereof represents a single bond, while the other of the two represents methyl or hydrogen, and one of the two $R_1$ on the right side thereof represents a single bond, while the other of the two represents methyl or hydrogen. Further, in the structure unit (II), it is preferred that one of the two $R_1$ represents a single bond, while the other of the two represents methyl or hydrogen.

According to this invention, multiple R' may be the same as or different from one another, preferably the same as one another, and preferably each independently selected from the group consisting of hydrogen and methyl, more preferably hydrogen.

According to this invention, $R_2$ preferably represents a $C_{5-12}$ linear or branched alkyl, more preferably a $C_{8-12}$ linear or branched alkyl, for example, octyl, decyl, nonyl, undecyl or dodecyl, especially a linear octyl, decyl, nonyl, undecyl or dodecyl.

According to this invention, $R_3$ preferably represents a $C_{1-4}$ linear or branched alkyl, more preferably methyl or ethyl.

According to this invention, as the hydrocarbyl having a number-averaged molecular weight Mn of 300-3000, there is exemplified a hydrocarbyl obtained by removing from a polyolefin having a number-averaged molecular weight Mn of 300-3000 (especially from a terminal of the polyolefin molecular chain) one hydrogen atom, hereinafter referred to as polyolefin residue group. Herein, the number-averaged molecular weight Mn of the polyolefin or the polyolefin residue group is preferably 500-2000, more preferably 500-1500. As the polyolefin, there is exemplified a polyolefin produced by the homopolymerization of ethylene, propylene or a $C_4$-$C_{10}$ α-olefin (for example, n-butene, iso-butene, n-pentene, n-hexene, n-octene or n-decene) or by the copolymerization between two or more of these olefins, more preferably a polyisobutene (PIB).

According to this invention, multiple y may be the same as or different from one another, preferably the same as one another, preferably 2 or 3, more preferably 2. According to this invention, by "Mannich base comprising the structure unit (I) and the structure unit (II)" or the like, it means that the structure unit (I) and the structure unit (II) can be identified/detected to co-exist in the Mannich base. To this end, according to this invention, the Mannich base could be a compound of one kind, from the molecular structure of which, both of these two structure units could be detected or identified, which means that, these two structure units co-exist in the molecular structure of this compound. Or alternatively, according to this invention, the Mannich base may be a mixture of compounds of different kinds, with the only proviso that these two structure units could be detected or identified from this mixture. Under this circumstance, these two structure units may co-exist in the molecular structure of one single compound (as preferred by this invention), or be separately comprised in the molecular structure of different compounds. Or preferably, the Mannich base according to this invention may be a mixture of compounds of different kinds, wherein the mixture comprises at least one compound, in the molecular structure of which these two structure units co-exist. The detection or identification method to be used herein has been well known in this field, including but not limiting to $^1$H-NMR or gel permeation chromatography (GPC).

According to this invention, when co-existing in the molecular structure of a single compound, these two structure units could directly bond to each other by sharing the moiety

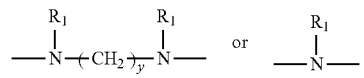

commonly comprised in both structures, or indirectly bond to each other at the position represented by the single bond or $R_1$ (only when $R_1$ represents a single bond) in each structure through a connecting unit

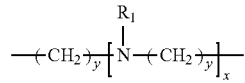

(Herein, y is as hereinbefore defined, and preferably the same as that in the structure unit (I) or the structure unit (II); $R_1$ is as hereinbefore defined; x is an integer of from 0 to 8, preferably an integer of from 0 to 3, more preferably 1).

According to this invention, in the Mannich base, the ratio by molar of the structure unit (I) and the structure unit (II) may be generally 1:1 to 1:15, preferably 1:1 to 1:8, more preferably 1:2 to 1:6, or 1:2 to 1:4.

According to an embodiment of this invention, the Mannich base is substantially consisted of the structure unit (I), the structure unit (II) and optionally the connecting unit. By "substantially" herein, it means that, any other structure unit or moiety than the structure unit (I), the structure unit (II) and the connecting unit, if does exist, only accounts for 5 mol % or less, preferably 2 mol % or less, more preferably 0.5 mol % or less, of the Mannich base as a whole, or only exists as unavoidable impurities.

According to an embodiment of this invention, the Mannich base is represented by the following formula (III).

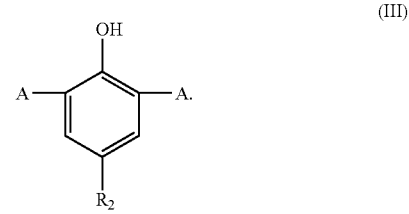

(III)

In the formula, multiple A may be the same as or different from one another, each independently selected from the group consisting of

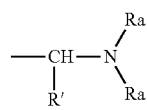

and hydrogen, with the proviso that at least one A represents

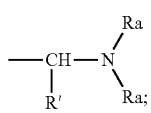

multiple R' may be the same as or different from one another, each independently selected from the group consisting of hydrogen and a $C_{1-6}$ linear or branched alkyl; multiple $R_a$ may be the same as or different from one another, each independently selected from the group consisting of hydrogen, a $C_{1-4}$ linear or branched alkyl and

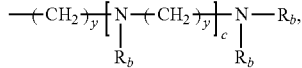

with the proviso that at least one $R_a$ represents

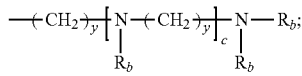

multiple $R_b$ may be the same as or different from one another, each independently selected from the group consisting of hydrogen,

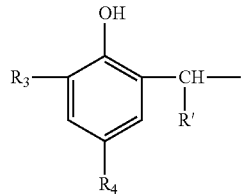

and a $C_{1-4}$ linear or branched alkyl, with the proviso that at least one $R_b$ represents

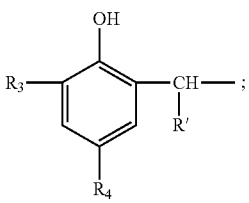

$R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5; multiple c may be the same as or different from one another, each independently selected from an integer of from 0 to 10.

According to this invention, multiple A is preferably the same as one another, more preferably all being

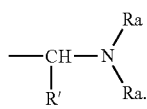

According to this invention, multiple R' may be the same as or different from one another (preferably the same as one another), and preferably each independently selected from the group consisting of hydrogen and methyl, more preferably hydrogen. According to this invention, multiple $R_a$ is preferably each independently selected from the group consisting of hydrogen, methyl and

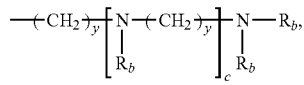

more preferably each independently selected from the group consisting of hydrogen and

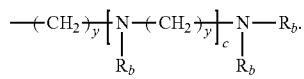

In each of the moiety

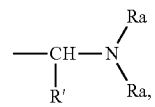

preferably one $R_a$ represents

while the other $R_a$ represents hydrogen or methyl, or both $R_a$ represent

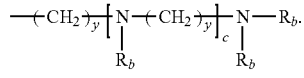

According to this invention, multiple $R_b$ is preferably each independently selected from the group consisting of hydrogen,

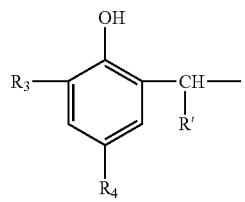

and methyl, more preferably each independently selected from the group consisting of hydrogen and

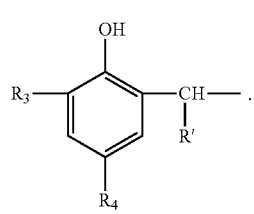

According to this invention, in the formula (III), preferably 1 to 15 out of all $R_b$ is

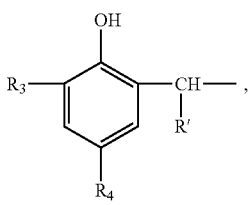

or 1 to 8 out of all $R_b$ is

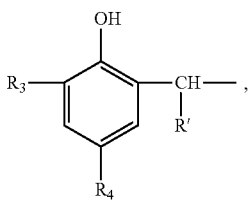

or 2 to 6 out of all $R_b$ is

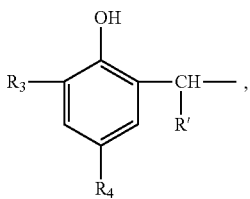

or 2 to 4 out of all $R_b$ is

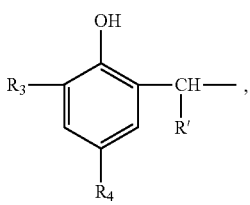

or 4 out of all $R_b$ is

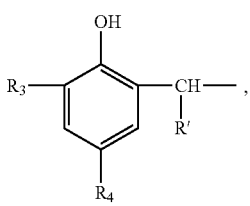

while remaining $R_b$ represents hydrogen or methyl.

According to this invention, $R_2$ preferably represents a $C_{5-12}$ linear or branched alkyl, more preferably a $C_{8-12}$ linear or branched alkyl, for example, octyl, decyl, nonyl, undecyl or dodecyl, especially a linear octyl, decyl, nonyl, undecyl or dodecyl.

According to this invention, $R_3$ preferably represents a $C_{1-4}$ linear or branched alkyl, more preferably methyl or ethyl.

According to this invention, as the hydrocarbyl having a number-averaged molecular weight Mn of 300-3000, there is exemplified a hydrocarbyl obtained by removing from a polyolefin having a number-averaged molecular weight Mn of 300-3000 (especially from a terminal of the polyolefin molecular chain) one hydrogen atom, hereinafter referred to as polyolefin residue group. Herein, the number-averaged molecular weight Mn of the polyolefin or the polyolefin residue group is preferably 500-2000, more preferably 500-1500. As the polyolefin, there is exemplified a polyolefin produced by the homopolymerization of ethylene, propylene or a $C_4$-$C_{10}$ α-olefin (for example, n-butene, iso-butene, n-pentene, n-hexene, n-octene or n-decene) or by the copolymerization between two or more of these olefins, more preferably a polyisobutene (PIB).

According to this invention, multiple y may be the same as or different from one another, preferably the same as one another, preferably 2 or 3, more preferably 2. According to this invention, multiple c may be the same as or different from one another, preferably each independently selected from an integer of from 2 to 5, more preferably 2 or 3.

According to this invention, the aforesaid Mannich base could be present, produced or used as individual (pure) compounds or as a mixture (at any ratio therebetween) thereof, both of which are acceptable to this invention.

According to this invention, the aforesaid Mannich base could be produced by e.g. the following process.

According to this invention, the process comprises the step of reacting a phenolic compound of the formula (V), a phenolic compound of the formula (VI), a polyalkylenepolyamine of the formula (VII) and a $C_1$-$C_7$ linear or branched saturated aliphatic aldehyde to conduct a Mannich reaction.

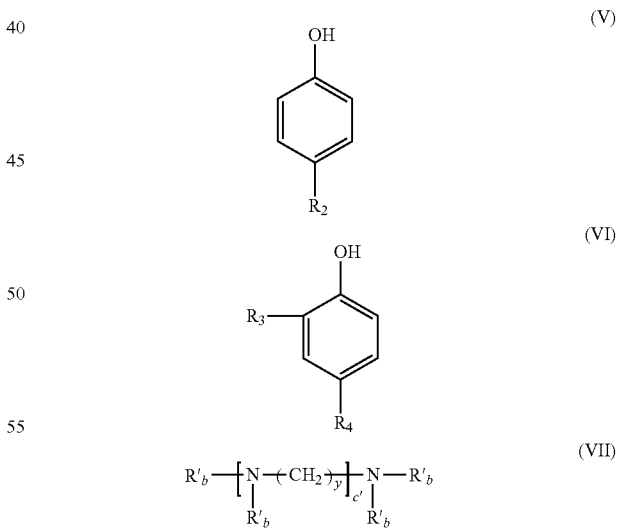

In these formulae, $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple $R_b'$ may be the same as or different from one another, each independently selected from the group consisting of hydrogen and a $C_{1-4}$ linear or branched alkyl, with the proviso that at least two of $R_b'$ represent hydrogen; y represents an integer of from 2 to 5; c' represents an integer of from 1 to 11.

According to this invention, $R_2$ preferably represents a $C_{5-12}$ linear or branched alkyl, more preferably a $C_{8-12}$ linear or branched alkyl, for example, octyl, decyl, nonyl, undecyl or dodecyl, especially a linear octyl, decyl, nonyl, undecyl or dodecyl.

According to this invention, $R_3$ preferably represents a $C_{1-4}$ linear or branched alkyl, more preferably methyl or ethyl.

According to this invention, as the hydrocarbyl having a number-averaged molecular weight Mn of 300-3000, there is exemplified a hydrocarbyl obtained by removing from a polyolefin having a number-averaged molecular weight Mn of 300-3000 (especially from a terminal of the polyolefin molecular chain) one hydrogen atom, hereinafter referred to as polyolefin residue group. Herein, the number-averaged molecular weight Mn of the polyolefin or the polyolefin residue group is preferably 500-2000, more preferably 500-1500.

In the context of this invention, depending on the nature of the starting polyolefin or the process for producing the starting polyolefin, the polyolefin residue group may represent a saturated chain (presenting as a long alkyl chain), or may contain certain amounts of ethylenic double bond along the polymer chain (for example, those remained or produced from the production thereof), which is acceptable to this invention and will not (significantly) compromise the performance of this invention. For this reason, it is unnecessary to specify herein at what amount this ethylenic double bond may be. As the polyolefin, there is exemplified a polymer produced by the homopolymerization of ethylene, propylene or a $C_4$-$C_{10}$ α-olefin (for example, n-butene, iso-butene, n-pentene, n-hexene, n-octene or n-decene) or that produced by the copolymerization between two or more of these olefins, more preferably a polyisobutene (PIB).

According to this invention, the phenolic compound of the formula (VI) could be produced by in the presence of an alkylating catalyst, reacting a phenolic compound of the formula (IV) with the polyolefin having a number-averaged molecular weight Mn of 300-3000 (preferably 500-2000, more preferably 500-1500) to conduct an alkylation reaction. Of course, the phenolic compound of the formula (VI) could be commercially available.

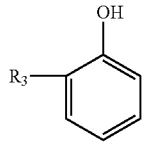

(IV)

In this formula, $R_3$ is as defined in the formula (VI), more preferably methyl.

According to this invention, the polyolefin is preferably one produced by the homopolymerization of ethylene, propylene or a $C_4$-$C_{10}$ α-olefin or that produced by the copolymerization between two or more of these olefins. As the $C_4$-$C_{10}$ α-olefin, there is exemplified n-butene, iso-butene, n-pentene, n-hexene, n-octene and n-decene. According to this invention, at least 20 wt % (preferably at least 50 wt %, more preferably at least 70 wt %) of the polymer chain from these polyolefins comprises an ethylenic double bond at the terminal thereof. The ethylenic double bond generally presents in the form of high reactive vinylene or vinyl.

According to this invention, the polyolefin is more preferably polybutene. Unless otherwise specified, the term "polybutene" used herein covers any polymer produced by the homopolymerization of 1-butene or iso-butene, and any polymer produced by the copolymerization between two or more of 1-butene, 2-butene and iso-butene. The commercially available product thereof may contain other olefin unit(s) with a minor amount, which is acceptable by this invention.

According to this invention, the polyolefin is more preferably polyisobutene (PIB) or high reactive polyisobutene (HR-PIB). In this polyisobutene, at least 20 wt % (preferably at least 50 wt %, more preferably at least 70 wt %) of the total terminal ethylenic double bond is provided by methyl vinylene.

As the alkylating catalyst, there is exemplified one or more selected from a Lewis acid catalyst, or specifically, from aluminium trichloride, boron trifluoride, tin tetrachloride, titanium tetrabromide, boron trifluoride•phenol, boron trifluoride•alcohol complex and boron trifluoride•ether complex, preferably boron trifluoride•diethyl ether complex and/or boron trifluoride•methanol complex. As the alkylating catalyst, a commercially available one could be used as such.

According to this invention, in the alkylation reaction, the ratio by molar between the polyolefin, the phenolic compound of the formula (IV) and the alkylating catalyst, for example, could be 1:1-3:0.1-0.5, preferably 1:1.5-3:0.1-0.4, most preferably 1:1.5-3:0.2-0.4, but not limiting thereto.

According to this invention, the reaction duration of the alkylation reaction, for example, may be generally 0.5 h-10 h, preferably 1 h-8 h, most preferably 3 h-5 h, but not limiting thereto.

According to this invention, the reaction temperature of the alkylation reaction, for example, may be generally 0 to 200 degrees centigrade, preferably 10 to 150 degrees centigrade, most preferably 20 to 100 degrees centigrade, but not limiting thereto.

According to this invention, the alkylation reaction could be conducted in the presence of a solvent. As the solvent, there is exemplified a $C_{6-10}$ alkane (for example, hexane, heptane, octane, nonane or decane), preferably hexane and heptane, more preferably hexane.

According to this invention, upon completion of the alkylation reaction, after removing the alkylating catalyst, any unreacted reactants and the optionally used solvent from the finally obtained reaction mixture by any way conventionally known in this field, the phenolic compound of the formula (VI) is obtained.

According to this invention, multiple $R_b'$ may be the same as or different from one another, preferably each independently selected from the group consisting of hydrogen and methyl. It is more preferred that the polyalkylenepolyamine of the formula (VII) has at least one of the multiple $R_b'$ at each terminal of the molecular chain thereof representing hydrogen respectively, which corresponds to the following formula (VII-1).

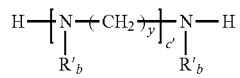

(VII-1)

In this formula, $R_b{}'$, y and c' are as defined in the formula (VII).

According to this invention, as the polyalkylenepolyamine, there is exemplified one or more selected from diethylenetriamine, triethylenetetramine, tetraethylenepentamine, pentaethylenehexamine, hexaethyleneheptamine, heptaethyleneoctamine, octaethylenenonamine, nonaethylenedecamine and decaethyleneundecamine, preferably diethylenetriamine.

According to this invention, the polyalkylenepolyamine could be a commercially available one or be produced by e.g. a reaction between ammonia and an alkane dihalide like an alkane dichloride.

According to this invention, y is preferably 2 or 3.

According to this invention, c' is preferably an integer of from 3 to 6, more preferably 3 or 4.

According to this invention, the $C_1$-$C_7$ linear or branched saturated aliphatic aldehyde is preferably acetaldehyde or formaldehyde, more preferably formaldehyde. As the formaldehyde, an aqueous solution of formaldehyde, polyformaldehyde or paraformaldehyde could be exemplified, without any specific limitation.

According to this invention, the process could be conducted in line with any one of the following ways.

Way (1) comprising the following steps:
the first step: reacting the phenolic compound of the formula (VI), the polyalkylenepolyamine of the formula (VII) and the $C_1$-$C_7$ linear or branched saturated aliphatic aldehyde at a reaction temperature of 50 to 200 degrees centigrade (preferably 60 to 150 degrees centigrade, most preferably 80 to 130 degrees centigrade) to conduct a Mannich reaction, to produce an intermediate; and
the second step: reacting the intermediate, the phenolic compound of the formula (V) and the $C_1$-$C_7$ linear or branched saturated aliphatic aldehyde at a reaction temperature of 40 to 200 degrees centigrade (preferably 60 to 150 degrees centigrade, most preferably 80 to 130 degrees centigrade) to conduct a Mannich reaction, so as to produce the Mannich base.

Way (2) comprising the following steps:
the first step: reacting the phenolic compound of the formula (V), the polyalkylenepolyamine of the formula (VII) and the $C_1$-$C_7$ linear or branched saturated aliphatic aldehyde at a reaction temperature of 40 to 200 degrees centigrade (preferably 60 to 150 degrees centigrade, most preferably 80 to 130 degrees centigrade) to conduct a Mannich reaction, to produce an intermediate; and
the second step: reacting the intermediate, the phenolic compound of the formula (VI) and the $C_1$-$C_7$ linear or branched saturated aliphatic aldehyde at a reaction temperature of 50 to 200 degrees centigrade (preferably 60 to 150 degrees centigrade, most preferably 80 to 130 degrees centigrade) to conduct a Mannich reaction, so as to produce the Mannich base.

Way (3) comprising a step of reacting the phenolic compound of the formula (V), the phenolic compound of the formula (VI), the polyalkylenepolyamine of the formula (VII) and the $C_1$-$C_7$ linear or branched saturated aliphatic aldehyde at a reaction temperature of 40 to 200 degrees centigrade (preferably 60 to 150 degrees centigrade, most preferably 80 to 130 degrees centigrade) to conduct a Mannich reaction, so as to produce the Mannich base.

According to this invention, from the standpoint of obtaining a Mannich base with a relatively higher purity, Way (1) is preferred.

According to this invention, in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.3-3:0.3-3.5, preferably 1:0.4-2:0.4-2.5, more preferably 1:0.5-1.5:0.5-2. There is no specific limitation as to the time duration of this step, which may be generally 1 h-10 h, preferably 2 h-8 h, most preferably 3 h-6 h.

According to this invention, in the second step of Way (1), the ratio by molar between the intermediate, the phenolic compound of the formula (V) and the $C_1$-$C_7$ linear or branched saturated aliphatic aldehyde is 1:0.2-1.5:0.2-2, preferably 1:0.3-1:0.2-1.5, more preferably 1:0.3-0.8:0.3-1.5. There is no specific limitation as to the time duration of this step, which may be generally 1 h-10 h, preferably 2 h-8 h, most preferably 3 h-6 h.

According to this invention, in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.5-2.5:1.5-3, preferably 1:1.7-2.5:1.7-2.8, more preferably 1:1.7-2.2:1.7-2.5. There is no specific limitation as to the time duration of this step, which may be generally 1 h-10 h, preferably 2 h-8 h, most preferably 3 h-6 h.

According to this invention, in the second step of Way (2), the ratio by molar between the intermediate, the phenolic compound of the formula (VI) and the $C_1$-$C_7$ linear or branched saturated aliphatic aldehyde is 1:1.5-3:1.5-3, preferably 1:1.7-2.5:1.7-3, more preferably 1:1.7-2.3:1.7-2.5. There is no specific limitation as to the time duration of this step, which may be generally 1 h-10 h, preferably 2 h-8 h, most preferably 3 h-6 h. According to this invention, in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1-5:1-3:2-8, preferably 1:1.5-4.5:1.5-2.5:3-7, more preferably 1:1.8-4.3:1.8-2.3:3.5-6.5. There is no specific limitation as to the time duration of Way (3), which may be generally 1 h-10 h, preferably 2 h-8 h, most preferably 3 h-6 h.

According to this invention, the aforesaid Mannich reaction could be conducted in the presence of a diluent and/or a solvent. As the diluent, there is exemplified one or more selected from polyolefins, mineral base oils and polyethers. As the solvent, there is exemplified a $C_{6-20}$ aromatic hydrocarbon (for example, toluene and xylene). Herein, toluene or xylene is preferred.

According to this invention, the diluent and/or the solvent could be added to the Mannich reaction at any stage thereof in any amount conventionally used in this field, for example, be added at the beginning of or during the first step in Way (1) and/or at the beginning of or during the second step in Way (1), at the beginning of or during the first step in Way (2) and/or at the beginning of or during the second step in Way (2), or at the beginning of or during Way (3), without any specific limitation.

According to this invention, as the mineral base oil, there is exemplified one or more selected from API Group I, API Group II or API Group III mineral lubricant base oils, preferably from mineral lubricant base oils having a viscosity of 20-120 centistokes (cSt) at 40 degrees centigrade and a viscosity index of at least 50 or more; more preferably from mineral lubricant base oils having a viscosity of 28-110 centistokes (cSt) at 40 degrees centigrade and a viscosity index of at least 80 or more.

According to this invention, as the polyolefin, there is exemplified one or more selected from a polyolefin produced by the homopolymerization of ethylene, propylene or a $C_4$-$C_{10}$ α-olefin or that produced by the copolymerization between two or more of these olefins, preferably from a poly α-olefin (PAO) having a viscosity of 2-25 centistokes (cSt) at 100 degrees centigrade (preferably that having a viscosity of 6-10 centistokes (cSt) at 100 degrees centigrade). Herein, as the $C_4$-$C_{10}$ α-olefin, there is exemplified n-butene, iso-butene, n-pentene, n-hexene, n-octene and n-decene. Further, the number-averaged molecular weight Mn of the polyolefin may be generally 500-3000, preferably 500-2500, most preferably 500-1500.

According to this invention, as the polyether, there is exemplified a polymer produced by a reaction between an alcohol and an epoxide. As the alcohol, there is exemplified ethylene glycol and/or 1,3-propylene glycol. As the epoxide, there is exemplified ethylene oxide and/or propylene oxide. Further, the number-averaged molecular weight Mn of the polyether may be generally 500-3000, preferably 700-3000, most preferably 1000-2500.

In general, the Mannich reaction is conducted under the protective atmosphere of an inert gas. As the inert gas, there is exemplified nitrogen gas or Ar gas, but without any limitation thereto.

According to this invention, upon completion of the process, after removing water and any solvent from the finally obtained reaction mixture by any way conventionally known in this field, a Mannich base is obtained.

In this context, this invention further relates to the Mannich base produced in line with the aforesaid process.

According to this invention, by the aforesaid process, as the reaction product, the Mannich base could be produced in the form of a single kind of Mannich base with relatively much higher purity (for example, 95% or more), or could be produced in the form of a mixture of two or more different Mannich bases, or could be produced in the form of a mixture of one or more Mannich base(s) with the aforesaid diluent (if any). All these forms are covered by this invention and identified as being effective and desirable in this invention. In view of this, in the context of this invention, these forms are all accepted or referred to as Mannich base of this invention without any discrimination therebetween. In this context, according to this invention, it is not absolutely necessary to further purify the reaction product, or to further isolate one or more specific Mannich base(s) from the reaction product. Of course, this purification or isolation may be preferred in some cases by this invention, however, is not absolutely necessary to this invention. Nevertheless, as the purification or isolation method, there is exemplified column chromatography or preparative chromatography.

The Mannich base of this invention is especially suitable for producing a detergent (as the major agent), especially a detergent for a fuel oil, which exhibits excellent deposit formation suppressing performance and excellent anticorrosion performance.

According to this invention, the detergent comprises any of the aforesaid Mannich base (or a mixture thereof at any ratio therebetween) or any Mannich base produced in line with the aforesaid process.

According to this invention, to produce the detergent, it is acceptable to further introduce the aforesaid diluent into the Mannich base. Herein, as the diluent, one kind or a mixture of two or more kinds at any ratio therebetween could be used. Of course, depending on the amount at which the diluent has been introduced into the Mannich base of this invention after production of same as aforesaid, the amount of diluent to be added could be reduced accordingly or even eliminated. In the latter case, the Mannich base per se could be used as a detergent without the need of adding any further diluent thereto, which is reasonable to a person skilled in the art.

In general, in the detergent of this invention, by weight, the Mannich base accounts for 10-70%, preferably 10-60%, most preferably 10-50%, of the total weight of the detergent.

According to this invention, to produce the detergent, it is acceptable to mix the Mannich base and the diluent (if any) at 20 to 60 degrees centigrade for 1 h-6 h.

The Mannich base or detergent of this invention is especially suitable for producing a fuel oil composition, which exhibits excellent deposit formation suppressing performance and excellent anticorrosion performance. In this context, this invention further relates to a fuel oil composition comprising any of the aforesaid Mannich bases (or a mixture thereof at any ratio therebetween), any of the Mannich base produced in line with the aforesaid process, or any of the aforesaid detergent, and a base fuel.

According to this invention, calculated as the Mannich base, on the basis of the total weight of the fuel oil composition, the amount of the Mannich base or that of the detergent may be generally 30-2000 mg/kg, preferably 50-2000 mg/kg, more preferably 50-1000 mg/kg.

According to this invention, as the base fuel, there is exemplified base fuels to be used in a spark ignition engine or a compression ignition engine, specifically, leaded or lead-free motor gasoline, aviation gasoline or diesel oil.

According to this invention, in addition to the Mannich base or the detergent, the fuel oil composition may further comprise other additional additive. As the additional additive, there is exemplified antiscaling agents, antioxidants, diluents, metal deactivators, dyes, markers, corrosion inhibitors, insecticides, antistatic agents, damping reduction agents, demulsifying agents, smoke reducing agents, antiicing additives, anti-knocking agents, lubricating additives and combustion adjuvants. As the additional additives, one kind or a mixture of two or more kinds at any ratio therebetween could be used, in an amount conventionally used in this field without any specific limitation.

EXAMPLE

The present invention is further illustrated by using the following examples, but not limiting to same.

Performances mentioned in Examples and Comparative Examples are determined as follows.

(1) Deposit Formation Suppressing Performance Evaluation

The deposit formation suppressing performance evaluation is conducted in line with a simulating test method for intake valve deposit of gasoline engine according to the Chinese National Standard No. GB19592-2004. According to this method, under the predetermined test conditions, a predetermined amount of the test sample is mixed with air via a nozzle and injected onto a deposit collector which has been weighted and heated to the test temperature beforehand, and then the deposit produced is weighted.

(2) Corrosion Evaluation

The corrosion evaluation is conducted in line with a test method for rust protection performance of gasoline detergent according to the Chinese National Standard No. GB/T19230.1-2003. According to this method, at a temperature of (38±1) degrees centigrade, a cylindrical test bar is totally immersed into a stirred mixture of 30 ml test sample and 30 ml distilled water to conduct the corrosion test for 4 h. The corrosion degree of the test bar is observed and scored as follows.

Slight corrosion: rust spots are not greater than 6 in number, each rust spot having a diameter of not more than 1 mm;
Moderate corrosion: rust spots are greater than 6 in number, but cover less than 5% of the surface area of the test bar;
Severe corrosion: rust spots cover greater than 5% of the surface area of the test bar. Table 1 lists chemicals to be used in Examples and Comparative Examples.

TABLE 1

| Chemicals | Specification | | Supplier |
|---|---|---|---|
| o-cresol | CP | ≥98.0% | Sinopharm Chemical Reagent Co., Ltd. |
| polyisobutene | HR-PIB | Mn = 1000 | Jilin Chemical Group Fine Chemicals Co., Ltd. |
| diethylenetriamine | CP | ≥98.0% | Beijing chemical plant |
| triethylenetetramine | CP | ≥95.0% | Sinopharm Chemical Reagent Co., Ltd. |
| tetraethylenepentamine | CP | ≥90.0% | Sinopharm Chemical Reagent Co., Ltd. |
| formaldehyde | AR | CH$_2$O: 37.0-40.0% | Sinopharm Chemical Reagent Co., Ltd. |
| polyformaldehyde | AR | ≥94.0% | Sinopharm Chemical Reagent Co., Ltd. |
| boron trifluoride -diethyl ether | CP | BF$_3$: 47.0-47.7% | Sinopharm Chemical Reagent Co., Ltd. |
| butanol | CP | ≥98.0 | Sinopharm Chemical Reagent Co., Ltd. |
| toluene | | ≥99.7 | Beijing chemical plant |
| xylene | AR | ≥99.0% | Beijing chemical plant |
| 4-tert-amyl phenol | | 99% | Alfa aesar (Tianjing) Chemical Co., Ltd. |
| 4-nonyl phenol | | | Tokyo Kasei kogyo Co. |
| 4-dodecyl phenol | | | Tokyo Kasei kogyo Co. |

Example 1

To a 500 ml four necked flask equipped with a stirrer, a thermometer, a condensing tube and a dropping funnel, there were added 34.93 g (0.323 mol) o-cresol, 6.88 g (0.048 mol) boron trifluoride•diethyl ether (as the alkylating catalyst), 100 ml n-hexane as the solvent and 161.61 g (0.162 mol) polyisobutene, at 80 degrees centigrade to react for 2 h. Upon completion of the reaction, the reaction mixture was washed once with a 5 wt % KOH aqueous solution, and then washed with hot water till neutral to remove any catalyst, and then vacuum distillated to remove any solvent and unreacted o-cresol, to obtain a polyisobutenyl o-cresol, having a hydroxyl value of 53.49 mgKOH/g. The hydroxyl value was determined by referring to the acetic anhydride method in GB/T7383-2007.

The reaction procedure can be illustrated as follows.

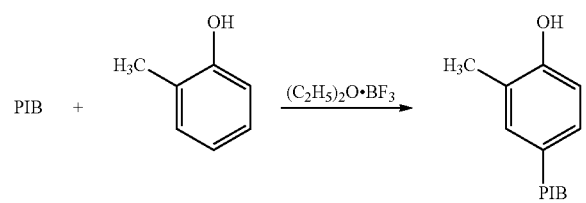

Figure 1:
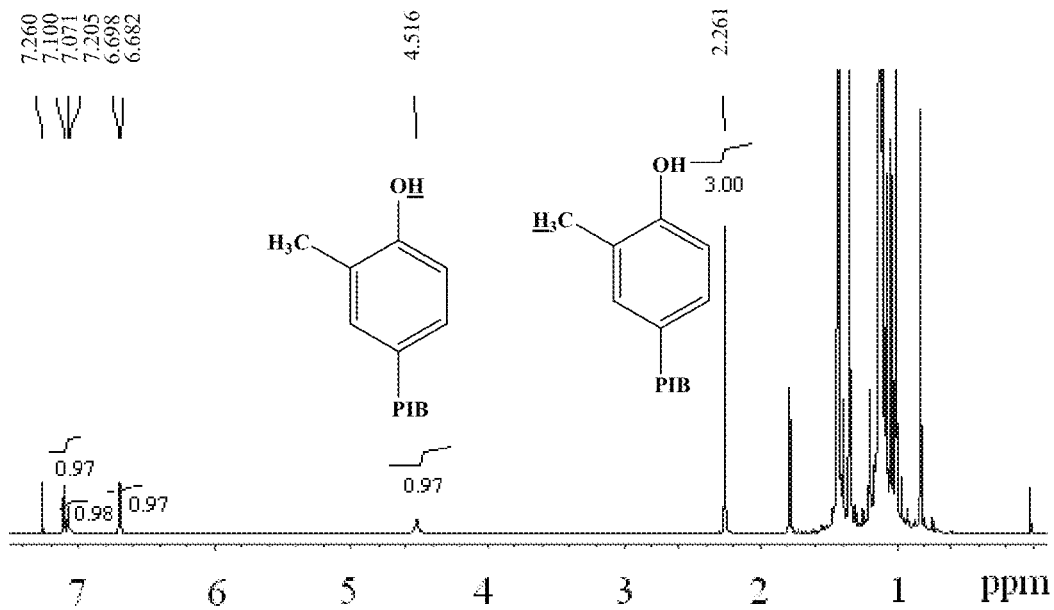
FIG. 1 illustrates the 1H NMR spectrum of the polyisobutenyl o-cresol produced in Example 1.
Figure 2:
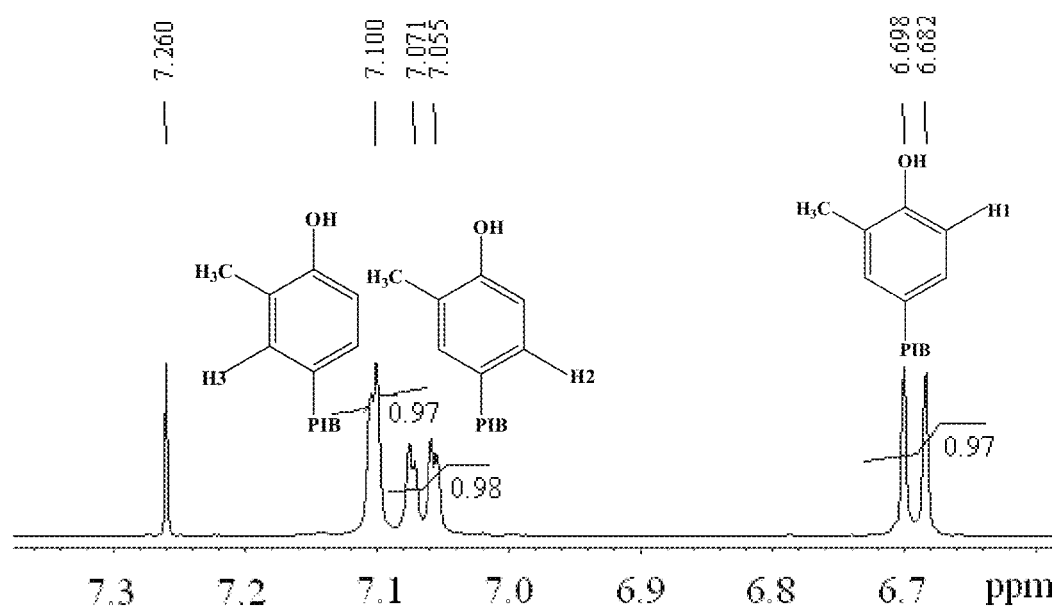
FIG. 2 illustrates the benzene ring region in the 1H NMR spectrum of the polyisobutenyl o-cresol produced in Example 1.

FIG. 1 illustrates the 1H NMR spectrum of the polyisobutenyl o-cresol produced in Example 1. FIG. 2 illustrates the benzene ring region in the 1H NMR spectrum of the polyisobutenyl o-cresol produced in Example 1. On the basis of FIGS. 1 and 2, it can be seen that: the peak at the chemical shift of 2.261 was identified as the characteristic peak of the hydrogen of methyl on the benzene ring of the polyisobutenyl o-cresol; the single peak at the chemical shift of 4.516 was identified as the characteristic peak of the hydrogen of the hydroxyl on the benzene ring of the polyisobutenyl o-cresol; the double peak at the chemical shift of 6.69 was identified as the characteristic peak of the hydrogen H1; the double peak at the chemical shift of 7.06 was identified as the characteristic peak of the hydrogen H2; the single peak at the chemical shift of 7.10 was identified as the characteristic peak of the hydrogen H3. If the integral of the hydrogen of methyl is defined as 3, the value of the integral ratio between the hydrogen on the benzene ring, the hydrogen of the hydroxyl and the hydrogen of methyl was calculated as 0.97:0.98:0.97:0.97:3.00, approximating to the theoretical value of 1:1:1:1:3. As can be seen from this NMR spectra analysis, the p-polyisobutenyl o-cresol was obtained as anticipated.

Example 2

Under the protective atmosphere of nitrogen gas, 47.16 g (0.045 mol) of the polyisobutenyl o-cresol produced in Example 1 was added to a 500 ml four necked flask equipped with a stirrer, a thermometer and a liquid separator, and then there were added 2.70 g (0.045 mol) ethylene diamine, 3.83 g (0.047 mol) formaldehyde, and there was added 47 ml toluene as the solvent, after reacted at 80 degrees centigrade for 1.5 h, cooled to the room temperature, there were added 4.97 g (0.0225 mol) 4-nonyl phenol, 3.83 g (0.047 mol) formaldehyde, reacted at 70 degrees centigrade for 1 h. Upon completion of the reaction, the reaction mixture was vacuum distillated to remove the solvent and any water produced, to obtain the final Mannich base.

The reaction procedure can be illustrated as follows.

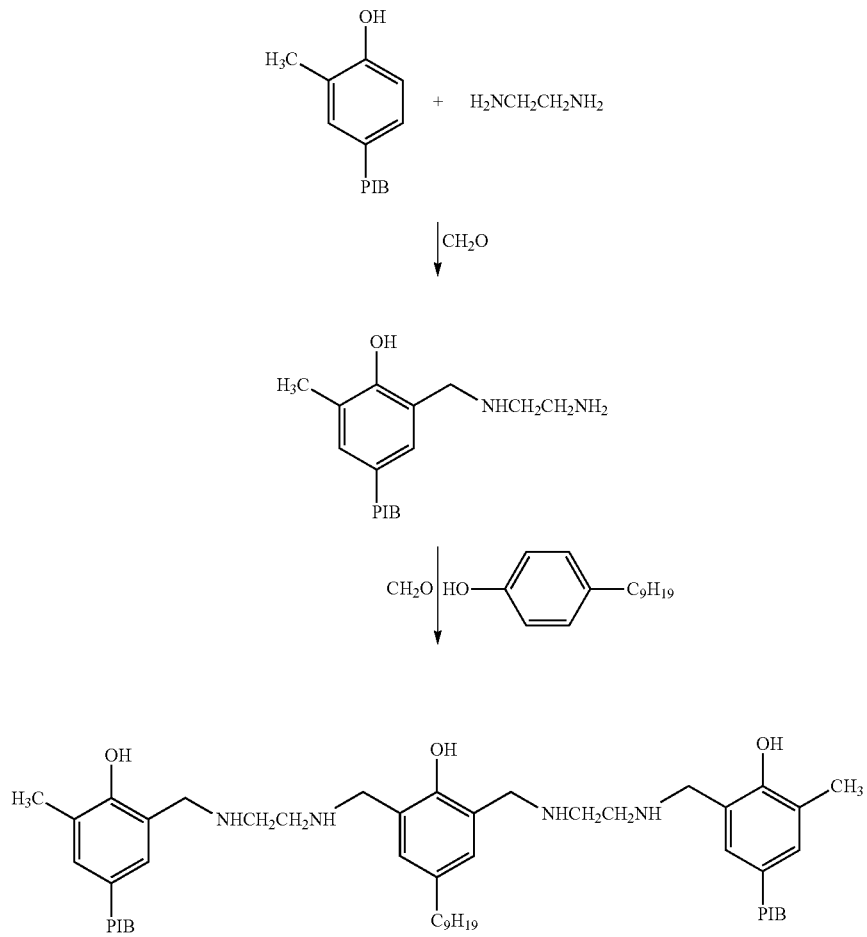

FIG. 3 compares the 1H NMR spectrum of the Mannich base produced in Example 2 with that of the polyisobutenyl o-cresol produced in Example 1. FIG. 4 compares the benzene ring region in the 1H NMR spectrum of the Mannich base produced in Example 2 and that of the polyisobutenyl o-cresol produced in Example 1. On the basis of FIGS. 3 and 4, it can be seen that: the peak at the chemical shift of 3.7 was identified as the characteristic peak of the hydrogen of methylene resulted from the carbonyl of formaldehyde; the peak at the chemical shift of 2.45 was identified as the characteristic peak of the hydrogen of the two methylene groups on ethylenediamine. Further, upon comparison between Example 2 and Example 1, it can be seen that: the hydrogen at the ortho position to the hydroxyl on the benzene ring of the polyisobutenyl o-cresol was consumed by the Mannich reaction, as a result, the characteristic peak of hydrogen in the benzene ring region was reduced from 3 to 2 in number. As can be seen from this NMR spectra analysis, the polyisobutenyl o-cresol was obtained as anticipated.

FIG. 5 illustrates the GPC spectrum of the polyisobutenyl o-cresol produced in Example 1.

FIG. 6 illustrates the GPC spectrum of the Mannich base produced in Example 2. As can be seen from FIG. 5 and FIG. 6, by doubling the starting materials for the Mannich reaction, the molecular weight of the produced Mannich base was increased accordingly, which indicates that the Mannich base had been obtained as anticipated.

Example 3

Under the protective atmosphere of nitrogen gas, 44.92 g (0.043 mol) of the polyisobutenyl o-cresol produced in Example 1 was added to a 500 ml four necked flask equipped with a stirrer, a thermometer and a liquid separator, and then there were added 4.64 g (0.043 mol) diethylenetriamine, 3.65 g (0.045 mol) formaldehyde, and there was added 47 ml xylene as the solvent, at 90 degrees centigrade to react for 1.5 h, and then cooled to the room temperature, there were added 5.64 g (0.0215 mol) 4-dodecyl phenol, 3.65 g (0.045 mol) formaldehyde, reacted at 70 degrees centigrade for 1 h. Upon completion of the reaction, the reaction mixture was vacuum distillated to remove the solvent and any water produced, to obtain the final Mannich base.

Example 4

Under the protective atmosphere of nitrogen gas, 53.37 g (0.051 mol) of the polyisobutenyl o-cresol produced in Example 1 was added to a 500 ml four necked flask equipped with a stirrer, a thermometer and a liquid separator, and then there were added 7.46 g (0.051 mol) triethylenetetramine, 4.38 g (0.054 mol) formaldehyde, and there was added 54 ml xylene as the solvent, at 100 degrees centigrade to react for 1.5 h, and then cooled to the room temperature, there were added 2.76 g (0.0255 mol) p-cresol, 4.38 g (0.054 mol) formaldehyde, reacted at 80 degrees centigrade for 1 h. Upon completion of the reaction, the reaction mixture was vacuum distillated to remove the solvent and any water produced, to obtain the final Mannich base.

Example 5

Under the protective atmosphere of nitrogen gas, 58.80 g (0.056 mol) of the polyisobutenyl o-cresol produced in Example 1 was added to a 500 ml four necked flask equipped with a stirrer, a thermometer and a liquid separator, and then there were added 2.89 g (0.028 mol) diethylenetriamine, 4.78 g (0.059 mol) formaldehyde, and there was added 53 ml toluene as the solvent, at 100 degrees centigrade to react for 1.5 h, then cooled to the room temperature, there were added 1.51 g (0.014 mol) p-cresol, 2.39 g (0.029 mol) formaldehyde, reacted at 80 degrees centigrade for 1 h. Upon completion of the reaction, the reaction mixture was vacuum distillated to remove the solvent and any water produced, to obtain the final Mannich base.

The reaction procedure can be illustrated as follows.

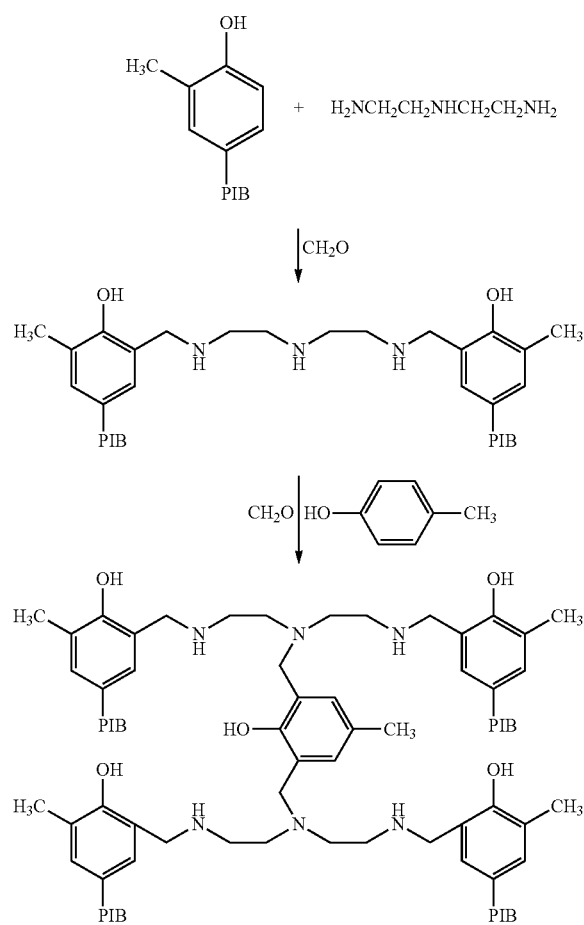

FIG. 7 illustrates the GPC spectrum of the Mannich base produced in Example 5. As can be seen from these FIG. 5, FIG. 6 and FIG. 7, by doubling the starting materials for the Mannich reaction, the molecular weight of the produced Mannich base was increased accordingly, which indicates that the Mannich base had been obtained as anticipated.

Example 6

Under the protective atmosphere of nitrogen gas, 40.01 g (0.038 mol) of the polyisobutenyl o-cresol produced in Example 1 was added to a 500 ml four necked flask equipped with a stirrer, a thermometer and a liquid separator, and then there were added 3.61 g (0.019 mol) tetraethylenepentamine, 3.25 g (0.040 mol) formaldehyde, and there was added 38 ml xylene as the solvent, after reacted at 80 degrees centigrade for 1.5 h, cooled to the room temperature, there were added 2.10 g (0.0095 mol) 4-nonyl phenol, 1.63 g (0.020 mol) formaldehyde, reacted at 70 degrees centigrade for 1 h. Upon completion of the reaction, the reaction mixture was vacuum distillated to remove the solvent and any water produced, to obtain the final Mannich base.

Example 7

Under the protective atmosphere of nitrogen gas, 51.33 g (0.049 mol) of the polyisobutenyl o-cresol produced in Example 1 was added to a 500 ml four necked flask equipped with a stirrer, a thermometer and a liquid separator, and then there were added 3.58 g (0.024 mol) triethylenetetramine, 1.53 g (0.051 mol) polyformaldehyde, and there was added 48 ml toluene as the solvent, after reacted at 90 degrees centigrade for 1.5 h, cooled to the room temperature, there were added 3.15 g (0.012 mol) 4-dodecyl phenol, 0.78 g (0.026 mol) polyformaldehyde, reacted at 70 degrees centigrade for 1 h. Upon completion of the reaction, the reaction mixture was vacuum distillated to remove the solvent and any water produced, to obtain the final Mannich base.

Example 8

Under the protective atmosphere of nitrogen gas, 2.86 g (0.048 mol) ethylenediamine and 6.24 g (0.024 mol) 4-dodecyl phenol were added to a 500 ml four necked flask equipped with a stirrer, a thermometer and a liquid separator, and then there was added 49 ml xylene as the solvent, at 50 degrees centigrade there was added 3.86 g (0.048 mol) formaldehyde solution and reacted for 0.5 h, and then heated to 110 degrees centigrade, further reacted for 2.5 h, cooled to 50 degrees centigrade, there was added 45.11 g (0.043 mol) of the polyisobutenyl o-cresol produced in Example 1, upon complete dissolution of the polyisobutenyl o-cresol, there was added 3.40 g (0.043 mol) formaldehyde solution, heated to 120 degrees centigrade, further reacted for 2 h. Upon completion of the reaction, the reaction mixture was vacuum distillated to remove the solvent and any water produced, to obtain the final Mannich base.

Example 9

Under the protective atmosphere of nitrogen gas, 5.70 g (0.039 mol) triethylenetetramine and 1.95 g (0.018 mol) p-cresol were added to a 500 ml four necked flask equipped with a stirrer, a thermometer and a liquid separator, and then there was added 49 ml xylene as the solvent, at 80 degrees centigrade there was added 1.41 g (0.047 mol) polyformaldehyde, gradually heated to 120 degrees centigrade and reacted for 2.5 h, and then there was added 40.91 g (0.039 mol) of the polyisobutenyl o-cresol produced in Example 1, after completely dissolved, there was added 1.20 g (0.040 mol) polyformaldehyde, further reacted for 2 h. Upon completion of the reaction, the reaction mixture was vacuum distillated to remove the solvent and any water produced, to obtain the final Mannich base.

Example 10

Under the protective atmosphere of nitrogen gas, 39.86 g (0.038 mol) of the polyisobutenyl o-cresol produced in Example 1, 2.46 g (0.041 mol) ethylenediamine, 3.06 g (0.019 mol) 4-tert-amyl phenol were added to a 500 ml four necked flask equipped with a stirrer, a thermometer and a liquid separator, and there was added 44 ml xylene as the solvent, heated to 80 degrees centigrade and stirred till a homogeneous reaction system was obtained, then there were added 3.18 g (0.106 mol) polyformaldehyde, and gradually heated to 130 degrees centigrade, reacted at this temperature for 4 h. Upon completion of the reaction, the reaction mixture was vacuum distillated to remove the solvent and any water produced, to obtain the final Mannich base.

Example 11

Under the protective atmosphere of nitrogen gas, 45.11 g (0.043 mol) of the polyisobutenyl o-cresol produced in Example 1, 4.16 g (0.022 mol) tetraethylenepentamine, 2.42 g (0.011 mol) 4-nonyl phenol were added to a 500 ml four necked flask equipped with a stirrer, a thermometer and a liquid separator, and there was added 50 ml toluene as the solvent, stirred till a homogeneous reaction system was obtained, heated to 45-50 degrees centigrade, and there was dropwise added 5.92 g (0.073 mol) formaldehyde solution over a period of 0.5 h, and after completion of this dropwise addition, further reacted for 0.5 h, and then gradually heated to 110 degrees centigrade, further reacted for 4 h. Upon completion of the reaction, the reaction mixture was vacuum distillated to remove the solvent and any water produced, to obtain the final Mannich base.

Comparative Example 1

Under the protective atmosphere of nitrogen gas, 51.27 g (0.049 mol) of the polyisobutenyl o-cresol produced in Example 1 was added to a 500 ml four necked flask equipped with a stirrer, a thermometer and a liquid separator, and then there were added 9.28 g (0.049 mol) tetraethylenepentamine, 4.77 g (0.059 mol) formaldehyde, and there was added 37 ml xylene as the solvent, at 80 degrees centigrade reacted for 1.5 h. Upon completion of the reaction, the reaction mixture was vacuum distillated to remove the solvent and any water produced, to obtain the final Mannich base.

Comparative Example 2

Under the protective atmosphere of nitrogen gas, 48.27 g (0.046 mol) of the polyisobutenyl o-cresol produced in Example 1 was added to a 500 ml four necked flask equipped with a stirrer, a thermometer and a liquid separator, and then there were added 3.36 g (0.023 mol) triethylenetetramine, 4.46 g (0.055 mol) formaldehyde, and there was added 45 ml toluene as the solvent, heated and stirred until homogeneous, and then there was dropwise added 4.46 g (0.055 mol) formaldehyde, at 80 degrees centigrade reacted for 1.5 h. Upon completion of the reaction, the reaction mixture was vacuum distillated to remove the solvent and any water produced, to obtain the final Mannich base.

Examples 12-21 and Comparative Examples 3-4

In line with the composition and the ratio specified in Table 2, each of the Mannich bases produced in Examples 2-11 and Comparative Examples 1 and 2 was mixed with a diluent respectively at 40 degrees centigrade for 2 h, to obtain the detergent of Examples 12-21 and Comparative Examples 3-4.

TABLE 2

| Detergent | Mannich base | Diluent | Ratio by weight of the Mannich base to the diluent |
|---|---|---|---|
| Example 12 | Example 2 | polyether[1] | 1:2 |
| Example 13 | Example 3 | PAO8[2] | 1:1 |
| Example 14 | Example 4 | 500SN[3] | 1:1.5 |
| Example 15 | Example 5 | polyisobutene[4] | 1:2 |
| Example 16 | Example 6 | polyether[1] | 1:1 |
| Example 17 | Example 7 | 500SN[3] | 1:1.5 |
| Example 18 | Example 8 | PAO8[2] | 1:1.5 |
| Example 19 | Example 9 | polyisobutene[4] | 1:1 |
| Example 20 | Example 10 | PAO8[2] | 1:1 |
| Example 21 | Example 11 | 500SN[3] | 1:1 |
| Comparative Example 3 | Comparative Example 1 | polyether[1] | 1:1 |
| Comparative Example 4 | Comparative Example 2 | 500SN[3] | 1:1.5 |

Note:
[1]DL1000, a polyether having a molecular weight of 1000, from Shanghai Dongda Polyurethane Co., Ltd.;
[2]FoxSyn PAO8, a Poly α-olefin, from Shanghai fukeshi Chemical Technology Co., Ltd.;
[3]500SN, a hydrogenated base oil, from Beijing Yanshan Petrochemical Co., Ltd.;
[4]PIB1000, a polyisobutene having a molecular weight of 1000, from Jilin Chemical Group Fine Chemicals Co., Ltd.

Examples 22-31 and Comparative Examples 5-6

In line with the composition and the ratio specified in Table 3, each of the detergents produced in Examples 12-21 and Comparative Examples 3 and 4 was mixed with a base gasoline respectively, to produce the fuel oil composition of Examples 22-31 and Comparative Examples 5-6, wherein on the basis of the total weight of each fuel oil composition, the detergent (calculated as the Mannich base) was added at an amount of 150 mg/kg in each case. The base gasoline to be used is a unleaded additive-free standard 93# gasoline. Further, the base gasoline without the detergent was used as Control. Each of the fuel oil compositions produced in Examples 22-31, the fuel oil compositions produced in Comparative Examples 5-6 and the Control was taken as the test sample, to conduct the deposit formation suppressing performance evaluation at a test temperature of 175 degrees centigrade. The results were shown in Table 3.

TABLE 3

| Fuel oil composition | Detergent | Detergent amount (mg/kg) | Deposit amount (mg) |
|---|---|---|---|
| Example 22 | Example 12 | 150 | 2.6 |
| Example 23 | Example 13 | 150 | 2.9 |
| Example 24 | Example 14 | 150 | 1.8 |
| Example 25 | Example 15 | 150 | 3.9 |
| Example 26 | Example 16 | 150 | 4.2 |
| Example 27 | Example 17 | 150 | 3.4 |
| Example 28 | Example 18 | 150 | 2.8 |
| Example 29 | Example 19 | 150 | 3.2 |

TABLE 3-continued

| Fuel oil composition | Detergent | Detergent amount (mg/kg) | Deposit amount (mg) |
|---|---|---|---|
| Example 30 | Example 20 | 150 | 3.9 |
| Example 31 | Example 21 | 150 | 4.5 |
| Comparative Example 5 | Comparative Example 3 | 150 | 7.8 |
| Comparative Example 6 | Comparative Example 4 | 150 | 7.3 |
| Control | — | — | 11.2 |

Examples 32-41 and Comparative Examples 7-8

In line with the composition and the ratio specified in Table 4, each of the Mannich bases produced in Examples 2-11 and Comparative Examples 1 and 2 was mixed with a base gasoline respectively, to produce the fuel oil composition of Examples 32-41 and Comparative Examples 7-8, wherein on the basis of the total weight of each fuel oil composition, the Mannich base was added at an amount of 100 mg/kg in each case. The base gasoline to be used is a unleaded additive-free standard 93# gasoline. Further, the base gasoline without the Mannich base was used as Control.

Each of the fuel oil compositions produced in Examples 32-41, the fuel oil compositions produced in Comparative Examples 7-8 and the Control was taken as the test sample, to conduct the corrosion evaluation. The results were shown in Table 4.

TABLE 4

| Fuel oil composition | Mannich base | Mannich base amount (mg/kg) | Corrosion degree |
|---|---|---|---|
| Example 32 | Example 2 | 100 | slight |
| Example 33 | Example 3 | 100 | slight |
| Example 34 | Example 4 | 100 | slight |
| Example 35 | Example 5 | 100 | slight |
| Example 36 | Example 6 | 100 | slight |
| Example 37 | Example 7 | 100 | slight |
| Example 38 | Example 8 | 100 | slight |
| Example 39 | Example 9 | 100 | slight |
| Example 40 | Example 10 | 100 | slight |
| Example 41 | Example 11 | 100 | slight |
| Comparative Example 7 | Comparative Example 1 | 100 | moderate |
| Comparative Example 8 | Comparative Example 2 | 100 | moderate |
| Control | — | — | severe |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A Mannich base, comprising the structure unit (I) and the structure unit (II):

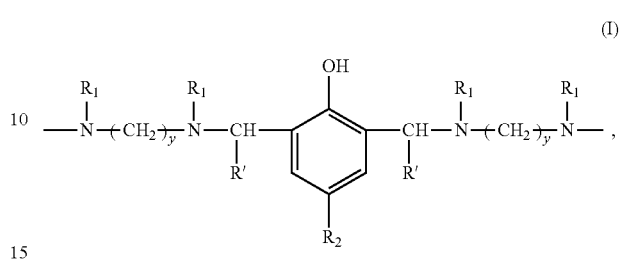

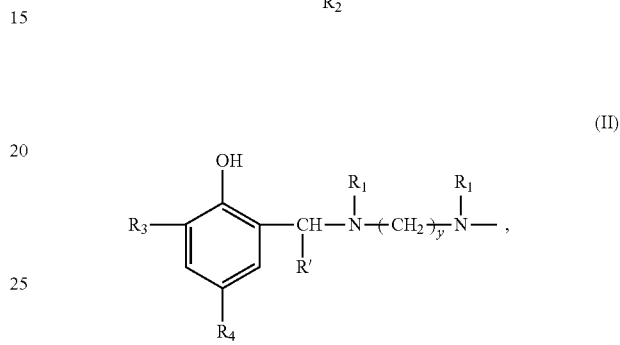

wherein, multiple $R_1$ may be the same as or different from one another, each independently selected from the group consisting of hydrogen, a $C_{1-4}$ linear or branched alkyl and a single bond; multiple R' may be the same as or different from one another, each independently selected from the group consisting of hydrogen and a $C_{1-6}$ linear or branched alkyl; $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5.

2. The Mannich base according to claim 1, represented by the following formula (III):

(III)

[structure showing phenol with OH, two A substituents ortho to OH, and $R_2$ para to OH]

wherein, multiple A may be the same as or different from one another, each independently selected from the group consisting of $$-\underset{R'}{\underset{|}{CH}}-N\underset{Ra}{\overset{Ra}{\diagdown}}$$

and hydrogen, with the proviso that at least one A represents

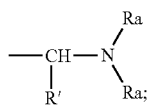

multiple R′ may be the same as or different from one another, each independently selected from the group consisting of hydrogen and a $C_{1-6}$ linear or branched alkyl; multiple $R_a$ may be the same as or different from one another, each independently selected from the group consisting of hydrogen, a $C_{1-4}$ linear or branched alkyl and

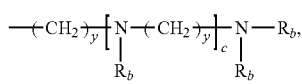

with the proviso that at least one $R_a$ represents

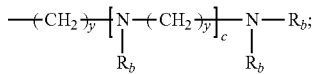

multiple $R_b$ may be the same as or different from one another, each independently selected from the group consisting of hydrogen,

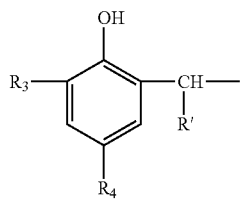

and a $C_{1-4}$ linear or branched alkyl, with the proviso that at least one $R_b$ represents

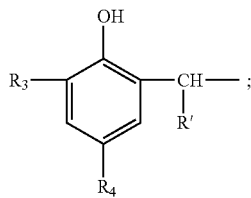

$R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5; multiple c may be the same as or different from one another, each independently selected from an integer of from 0 to 10.

3. A process for producing a Mannich base comprising the step of reacting a phenolic compound of the formula (V), a phenolic compound of the formula (VI), a polyalkylenepolyamine of the formula (VII) and a $C_1$-$C_7$ linear or branched saturated aliphatic aldehyde to conduct a Mannich reaction,

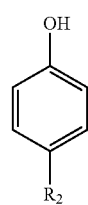

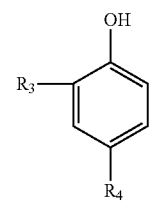

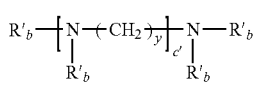

wherein, $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple $R_b'$ may be the same as or different from one another, each independently selected from the group consisting of hydrogen and a $C_{1-4}$ linear or branched alkyl, with the proviso that at least two of $R_b'$ are hydrogen; y represents an integer of from 2 to 5; c′ represents an integer of from 1 to 11.

4. The process for producing a Mannich base according to claim 3, which is conducted in line with any one of the following ways:

Way (1) comprising the following steps:
the first step: reacting the phenolic compound of the formula (VI), the polyalkylenepolyamine of the formula (VII) and the $C_1$-$C_7$ linear or branched saturated aliphatic aldehyde at a reaction temperature of 50 to 200 degrees centigrade to conduct a Mannich reaction, to produce an intermediate; and
the second step: reacting the intermediate, the phenolic compound of the formula (V) and the $C_1$-$C_7$ linear or branched saturated aliphatic aldehyde at a reaction temperature of 40 to 200 degrees centigrade to conduct a Mannich reaction, so as to produce the Mannich base, or Way (2) comprising the following steps:
the first step: reacting the phenolic compound of the formula (V), the polyalkylenepolyamine of the formula (VII) and the $C_1$-$C_7$ linear or branched saturated aliphatic aldehyde at a reaction temperature of 40 to 200 degrees centigrade to conduct a Mannich reaction, to produce an intermediate; and
the second step: reacting the intermediate, the phenolic compound of the formula (VI) and the $C_1$-$C_7$ linear or branched saturated aliphatic aldehyde at a reaction temperature of 50 to 200 degrees centigrade to conduct a Mannich reaction, so as to produce the Mannich base, or Way (3) comprising the step of reacting the phenolic compound of the formula (V), the phenolic compound of the formula (VI), the polyalkylenepolyamine of the formula (VII) and the $C_1$-$C_7$ linear or branched saturated aliphatic aldehyde at a reaction temperature of 40 to 200 degrees centigrade to conduct a Mannich reaction to produce the Mannich base.

5. The process for producing a Mannich base according to claim 4, wherein in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.3-3:0.3-3.5; in the second step of Way (1), the ratio by molar between the intermediate, the phenolic compound of the formula (V) and the $C_1$-$C_7$ linear or branched saturated aliphatic aldehyde is 1:0.2-1.5:0.2-2; in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.5-2.5:1.5-3; in the second step of Way (2), the ratio by molar between the intermediate, the phenolic compound of the formula (VI) and the $C_1$-$C_7$ linear or branched saturated aliphatic aldehyde is 1:1.5-3:1.5-3; in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1-5:1-3:2-8.

6. The process for producing a Mannich base according to claim 3, wherein the Mannich reaction is conducted in the presence of one or more diluent selected from the group consisting of polyolefins, mineral base oils and polyethers.

7. The process for producing a Mannich base according to claim 3, wherein the phenolic compound of the formula (VI) is produced by in the presence of an alkylating catalyst, reacting a phenolic compound of the formula (IV) with a polyolefin having a number-averaged molecular weight Mn of 300-3000 to conduct an alkylation reaction,

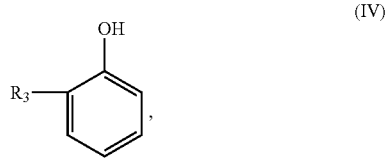

wherein, $R_3$ is as defined in claim 3.

8. A detergent comprising the Mannich base according to claim 1 or a Mannich base produced in line with the process according to claim 3, and one or more diluent selected from the group consisting of polyolefins, mineral base oils and polyethers.

9. The detergent according to claim 8, wherein by weight, the Mannich base accounts for 10-70% of the total weight of the detergent.

10. A fuel oil composition, comprising the Mannich base according to claim 1, a Mannich base produced in line with the process according to claim 3 or the detergent according to claim 8, and a base fuel, wherein calculated as the Mannich base, on the basis of the total weight of the fuel oil composition, the amount of the Mannich base or the detergent is 30-2000 mg/kg.

11. The Mannich base according to claim 1, wherein the ratio by molar of the structure unit (I) and the structure unit (II) is 1:1 to 1:15.

12. The Mannich base according to claim 2, wherein $R_2$ represents a $C_{5-12}$ linear or branched alkyl; multiple c may be the same as or different from one another, each independently selected from an integer of from 2 to 5.

13. The process for producing a Mannich base according to claim 5, wherein in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.5-1.5:0.5-2; in the second step of Way (1), the ratio by molar between the intermediate, the phenolic compound of the formula (V) and the $C_1$-$C_7$ linear or branched saturated aliphatic aldehyde is 1:0.3-0.8:0.3-1.5; in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.7-2.2:1.7-2.5; in the second step of Way (2), the ratio by molar between the intermediate, the phenolic compound of the formula (VI) and the $C_1$-$C_7$ linear or branched saturated aliphatic aldehyde is 1:1.7-2.3:1.7-2.5; in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1.8-4.3:1.8-2.3:3.5-6.5.

* * * * *